United States Patent
Shingu et al.

(10) Patent No.: US 6,620,147 B2
(45) Date of Patent: Sep. 16, 2003

(54) DISPOSABLE DIAPER AND PROCESS FOR MAKING THE SAME

(75) Inventors: Yoshikazu Shingu, Kagawa-ken (JP); Hirotomo Mukai, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/871,017

(22) Filed: May 31, 2001

(65) Prior Publication Data

US 2002/0002359 A1 Jan. 3, 2002

(30) Foreign Application Priority Data

Jun. 19, 2000 (JP) .......................................... 2000-183703

(51) Int. Cl.[7] .............................................. A61F 13/15
(52) U.S. Cl. ........................ 604/391; 604/386; 604/387
(58) Field of Search ................................ 604/391, 389, 604/385.01, 385.28, 387, 386

(56) References Cited

U.S. PATENT DOCUMENTS

| | | | | |
|---|---|---|---|---|
| 4,237,890 A | * | 12/1980 | Laplanche | .................. 128/287 |
| 4,704,117 A | * | 11/1987 | Mitchell | ..................... 604/391 |
| 5,049,145 A | * | 9/1991 | Flug | ............................ 604/391 |
| 5,053,028 A | * | 10/1991 | Zoia et al. | ............... 604/385.1 |
| 5,100,399 A | * | 3/1992 | Janson et al. | ............... 604/386 |
| 5,318,555 A | * | 6/1994 | Siebers et al. | .............. 604/390 |
| 5,383,872 A | | 1/1995 | Roessler et al. | |
| 5,961,761 A | | 10/1999 | Heindel et al. | |
| 5,997,981 A | | 12/1999 | McCormack et al. | |
| 6,213,991 B1 | * | 4/2001 | Kling et al. | ........... 604/385.01 |

FOREIGN PATENT DOCUMENTS

EP  0 793 953 A2  9/1997

OTHER PUBLICATIONS

European search report mailed Feb. 1, 2002.

* cited by examiner

Primary Examiner—Weilun Lo
Assistant Examiner—Jacqueline Stephens
(74) Attorney, Agent, or Firm—Butzel Long

(57) ABSTRACT

A disposable diaper that includes a pair of wings formed with a nonwoven fabric. Each of the wings is formed on its circumferentially outer edge with fastener sections each including a male member as a component of so-called mechanical fastener. The fastener sections are folded back onto inner surface of the wing so that only a portion of hooks constituting the male member are releasably engaged with the component fibers of the nonwoven fabric protruding toward the hooks.

4 Claims, 3 Drawing Sheets

DISPOSABLE DIAPER AND PROCESS FOR MAKING THE SAME

BACKGROUND OF THE INVENTION

This invention relates to a disposable diaper and a process for making the same.

Conventional disposable diapers are formed in its rear waist region with a pair of wings made of a nonwoven fabric. Such wings are formed with fastener sections serving to connect the front and rear waist regions to each other. The fastener sections are provided on inner surfaces thereof with adhesive zones or male members as component of mechanical fasteners so that these adhesive zones or male members may be releasably anchored on the front waist region and thereby the front and rear waist regions may be connected to each other.

The fastener sections, if they are arranged so as to extend outward from outer side edges of the wings in the circumferential direction, will be preferably folded back onto the inner surfaces of the respective wings and releasably anchored in order to avoid that these protruding fastener sections might adversely stand in the course from production of the diaper to actual use of the diaper by the consumer. However, use of the male member as the component of the mechanical fastener is often accompanied with an anxiety that the male member could not be anchored at a desired peel strength on the nonwoven fabric forming the inner surface of the wing and might be unintentionally separated apart from the wing in the course of handling the diaper.

SUMMARY OF THE INVENTION

Objects of this invention include providing a process for ensuring that fastener sections provided with male members are reliably and releasably anchored on the inner surfaces of respective wings of disposable diapers, and a disposable diaper made using such process.

According to this invention, there is provided a disposable diaper and a process for making the same.

According to one aspect of this invention, the disposable diaper includes a liquid-pervious topsheet, a liquid-impervious backsheet and a liquid-absorbent core disposed between these two sheets so as to configure a front waist region, a rear waist region and a crotch region extending between these two waist regions in a longitudinal direction of the diaper wherein the rear waist region is formed on transversely opposite sides thereof with wings extending outward in a circumferential direction intersecting the longitudinal direction and the wings are formed with fastener sections extending outward in the circumferential direction and provided on inner surfaces thereof with male members as components of mechanical fasteners.

According to this invention each of the wings has inner and outer surfaces of which at least the inner surface is formed with a nonwoven fabric; each of the fastener sections is folded a back onto the inner surface of the wing so that the male member may be opposed to the nonwoven fabric of the inner surface and a plurality of hooks forming the male member may be releasably engaged only with a portion of fibers forming the nonwoven fabric protruding from the inner surface toward the male member.

According to another aspect of this invention, there is further provided a process for making a disposable diaper composed of a front waist region, a rear waist region and a crotch region extending between these two waist regions in the longitudinal direction of the diaper, the rear waist region being formed on transversely opposite sides thereof with wings extending outward in a circumferential direction intersecting the longitudinal direction, the wings being formed with fastener sections extending outward in the circumferential direction and the fastener sections being folded back, with inner surfaces thereof inside, in the circumferential direction so that male members of mechanical fasteners attached to inner surfaces of the fastener sections may be in contact with inner surfaces of the wings.

The process according to this invention comprises steps of: forming inner and outer surfaces, at least said inner surfaces of said wings by nonwoven fabric; and locally pressing the nonwoven fabric from the outer surface toward the inner surface thereof in its region being in contact with the male members so that fibers forming the nonwoven fabric may partially protrude toward the male members and be releasably engaged only with a portion of a plurality of hooks forming the male members.

DETAILED DESCRIPTION OF THE PREFERRED EMBODIMENT

Details of a disposable diaper according to this invention will be more fully understood from the description given hereunder with reference to the accompanying drawings.

Figure 1:
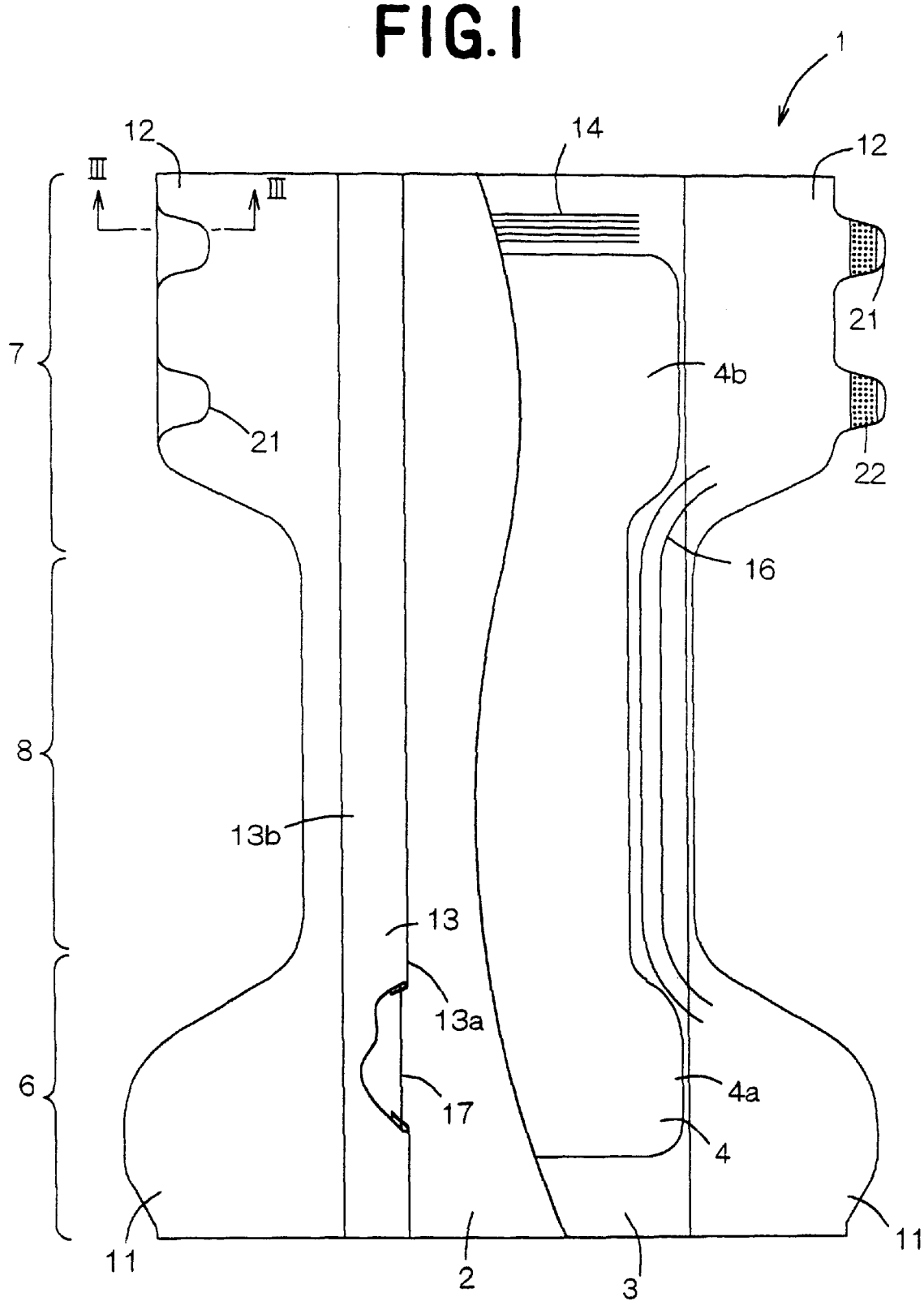
FIG. 1 is a plan view showing an inner side of a disposable diaper as partially broken away.
Figure 2:
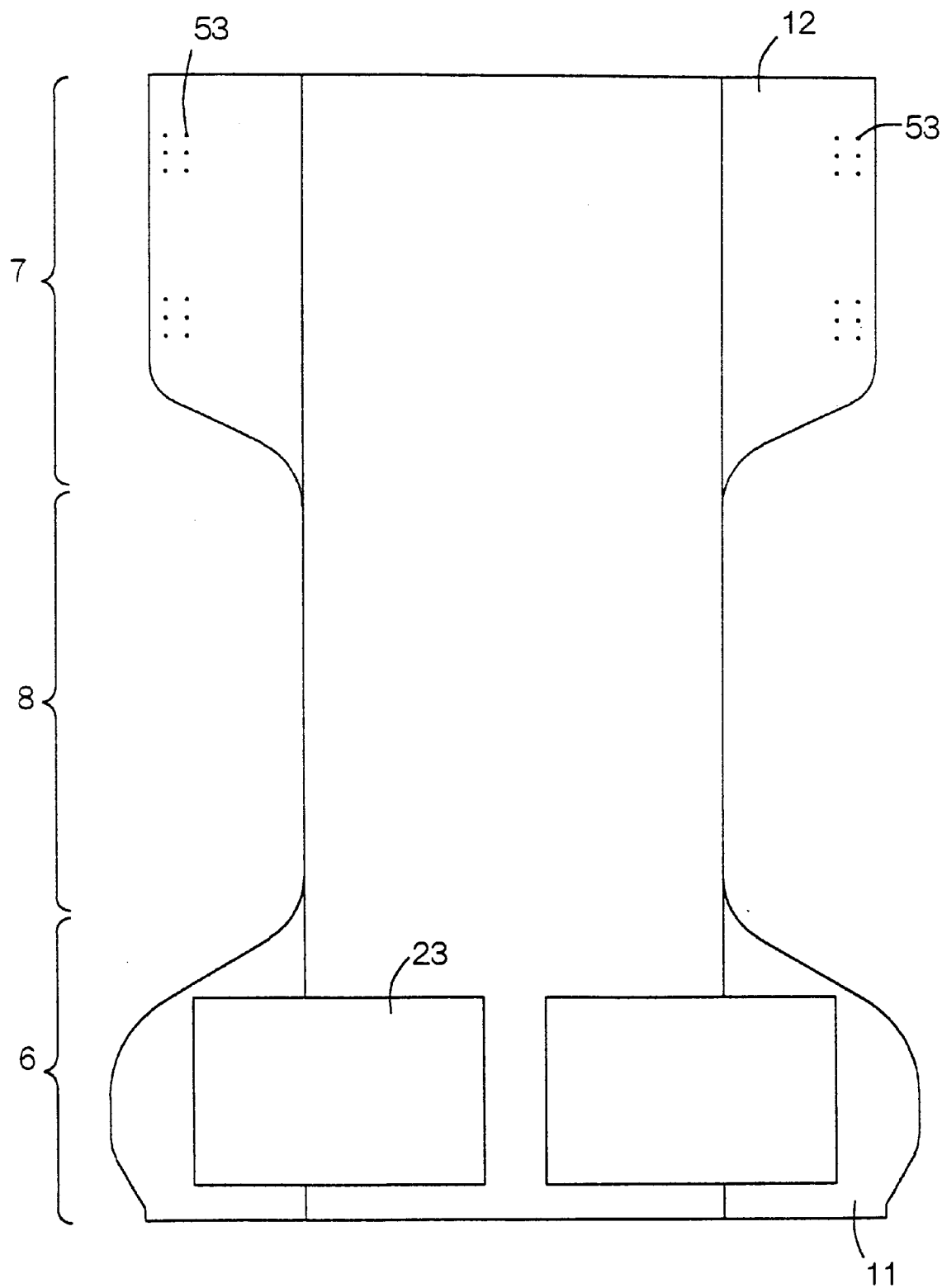
FIG. 2 is a plan view showing an outer side of the disposable diaper.

FIG. 1 is a plan view showing an inner side of a diaper 1 as partially broken away and FIG. 2 is a plan view showing an outer side of this diaper 1. The diaper 1 has a liquid-pervious topsheet 2, a liquid-impervious backsheet 3 and a liquid-absorbent core 4 disposed between these two sheets 2, 3. The diaper 1 is longitudinally (i.e., vertically as viewed in these figures) composed of a front waist region 6, a rear waist region 7 and a crotch region 8 extending between these two waist regions 6, 7. The front and rear waist regions 6, 7 are respectively formed with front wings 11 and rear wings 12 extending circumferentially outward from transversely opposite side edges thereof. Along an outer end of the rear waist region 7, a plurality of elastic members 14 extend circumferentially of the region 7 to be associated with a waist-opening. The crotch region 8 is provided along transversely opposite side edges thereof with a plurality of elastic members 16 extending longitudinally of the region 8 to be associated with respective leg-openings. These elastic members 14, 16 are disposed between the top- and backsheets 2, 3 or separately prepared sheets bonded to these top- and backsheets 2, 3, respectively, to extend and bonded under tension to one of these sheets.

A pair of ribbon-like barrier cuffs 13 longitudinally extend on the inner surface of the diaper 1 in parallel to transversely opposite side edges of the diaper 1, respectively. Each of the barrier cuffs 13 has its outer side edge portion 13b as well as its longitudinally opposite end portions fixed to the inner surface of the diaper 1 and its inner side edge portion 13a not fixed to the inner surface of the diaper 1. More specifically, the inner side edge portion 13a is folded back in envelope-like manner to wrap a longitudinally extending elastic member 17 biasing the cuff 13 to rise on the inner surface of the diaper 1 (See FIG. 5). The elastic member 17 is bonded under tension to the inner surface of the barrier cuff 13 at least at the longitudinally opposite end portions so that contraction of the elastic member 17 may cause the barrier cuff 13 to rise on the inner surface of the diaper 1 as the diaper 1 is put on a wearer's body. Thus, such barrier cuffs 13 are adapted to form a pair of pockets (not shown) opening inwardly of the diaper 1 and thereby to prevent body fluids from leaking.

The transversely opposite side edges of the rear wing 12 partially extend circumferentially outward to form respective pairs of fastener sections 21 spaced apart from each other vertically as viewed in FIGS. 1 and 2. Each of the fastener sections 21 is provided on its inner surface with a male member 22 as a component of a mechanical fastener so as to extend longitudinally thereof. FIG. 1 shows the left side fastener sections 21 as folded onto the inner surface of the rear wing 12 and the right side fastener sections 21 as extending circumferentially outward. As will be seen in FIG. 2, all the fastener sections 21 are folded onto the inner surfaces of the wing 12. These fastener sections 21 can be releasably anchored on the associated female members 23 at appropriate positions thereof to connect the front and rear waist regions 6, 7 to each other. These female members 23 are components of the mechanical fasteners and attached to the outer surface of the front waist region 6.

Figure 3:
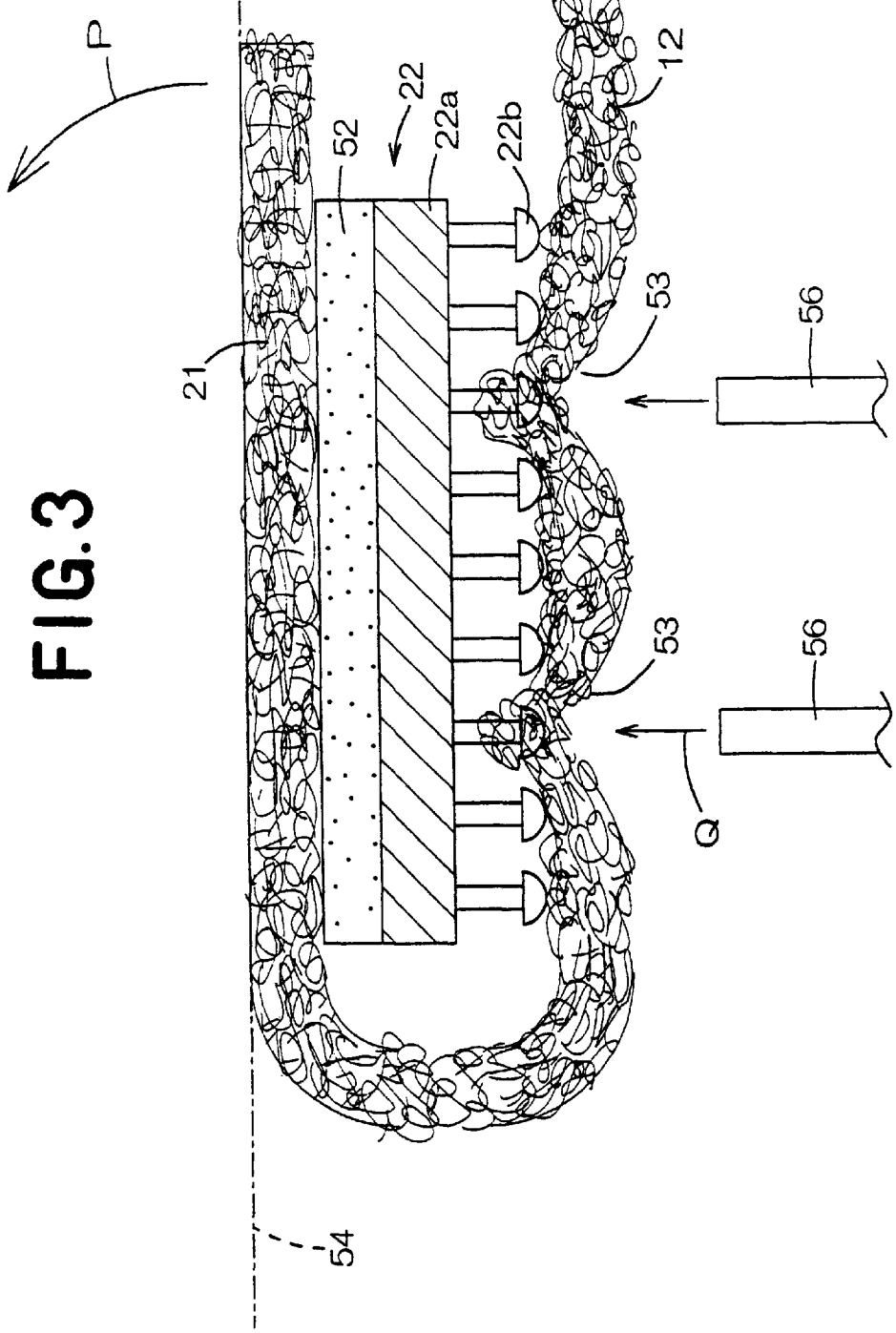
FIG. 3 is a sectional view taken along a line III—III in FIG. 1.

FIG. 3 is a sectional view taken along a line III—III in FIG. 1. Both the rear wings 12 and the fastener sections 21 extending therefrom are formed by a nonwoven fabric made of thermoplastic synthetic fibers 51. The male member 22 of the mechanical fastener comprises a base plate 22a and a plurality of hooks 22b protruding from the plate 22a downward as viewed in FIG. 3 and firmly bonded to the inner surface of the fastener section 21 by means of adhesive 52. So long as the fastener section 21 is folded back onto the inner surface of the rear wing 12, distal ends of the hooks 22b are in contact with the inner surface of the wing 12. The rear wing 12 includes a region 53 in which the rear wing 12 is locally pressed from the outer surface toward the inner surface of the region (i.e., pressed upward as viewed in FIG. 3). As has been described above, the distal ends of a plurality of hooks 22b are in contact with the inner surface of the wing 12. The fibers 51 protrude from the outer surface toward the inner surface of the nonwoven fabric and selectively engage only the hooks 22b lying immediately above the region 53 as the region 53 is pressed from the outer surface toward the inner surface. This engagement holds the fastener section 21 in its folded state. At least one, preferably two or more regions 53 in which a plurality of hooks 22b are in contact with the inner surface of the wing 12 may be provided at an intercentral distance of at least 5 mm in order to prevent an anxiety that the fastener sections 21 might be unintentionally disengaged from the wings 12. To peel the fastener sections 21 off from the respective wings 12, the distal ends of the fastener sections 21 may be grasped and pulled upward in a direction as indicated by an arrow P and thereby the hooks 22b may be disengaged from the fibers 51.

To form the rear wings 12 with the regions 53, the plates 54 may be applied from above as viewed in FIG. 3 upon the folded fastener sections 21 and then pins 56 each having a diameter in the order of 0.2~2.5 mm may be pressed from below as viewed in FIG. 3 in a direction as indicated by an arrow Q against the outer surfaces of the respective wings 12 (See FIG. 2 also). When it is desired to obtain a relatively firm engagement between the hooks 22b and the fibers 51, the pins 56 are preferably heated to a temperature sufficiently high to soften or melt the fibers 51. An intercentral distance between each pair of the adjacent regions 53 is at least 5 mm, more preferably in a range of 7~13 mm.

A strength with which the fastener section 21 constructed in this manner and the rear wing 12 are engaged with each other, in other words, a force required to peel the fastener section 21 off from the wing 12 may be adjusted by increasing or decreasing the number of the regions 53 in which the fibers 51 protrude.

In the diaper 1 illustrated as a typical embodiment of this invention, the front wings 11 and the side portions of the crotch region 8 are formed with a nonwoven fabric similarly to the rear wings 12. As the component fibers 51 of the nonwoven fabric, various types of thermoplastic synthetic fibers such as polyproplylene fiber or crimped conjugated fiber comprising polypropylene as a core and polyethylene as a sheath may be used at a basis weight of 30~200 g/m$^2$. This invention enabling the fastener sections 21 to be reliably held in folded state by engaging the fastener sections 21 with the fibers 51 is particular useful for an adult disposable diaper which uses relatively large fastener sections 21.

This invention is not limited to the specific embodiment as illustrated but the other embodiments are also possible, for example, an alternative embodiment in which the rear waist region 7 is replaced by the front waist region 6 or vice versa.

In the disposable diaper according to this invention, after the fastener sections extending outward from the rear wings in the circumferential direction have been folded back onto the inner surfaces of the respective wings, only the fibers locally protruding from the outer surfaces toward the inner surfaces in the regions of the wings are selectively engaged with portions of the fastener sections' male members. With an advantageous consequence, the fastener sections can be reliably held in folded state and a strength with which the fastener sections are engaged with the respective wings can be adjusted by increasing or decreasing the number of the regions in which the fibers locally protrude.

What is claimed is:

1. A disposable diaper comprising:
   a liquid-pervious topsheet;
   a liquid-impervious backsheet;
   a liquid-absorbent core disposed between the liquid-pervious topsheet and the liquid-impervious backsheet;
   a front waist region;
   a rear waist region;
   a crotch region extending between the front waist region and the rear waist region in a longitudinal direction of the diaper; and
   first wings formed on transversely opposite sides of the rear waist region and extending outward in a transverse direction intersecting said longitudinal direction,
   said first wings being formed with fastener sections extending outward in said transverse direction and provided on inner surfaces thereof with male mechanical fastener members,
   each of said first wings having inner and outer surfaces of which at least said inner surface comprises a nonwoven fabric formed from a plurality of fibers,
   each of said fastener sections being folded back onto the inner surface of a first wing to which it is formed so that said male mechanical fastener members thereof are opposed to said nonwoven fabric of said inner surface and a plurality of hooks forming said male mechanical fastener members may be releasably engaged with portions of the plurality of fibers forming said nonwoven fabric which protrude from said inner surface toward said male mechanical fastener members.

2. A process for making a disposable diaper having a front waist region, a rear waist region, a crotch region extending between the front and rear waist regions in a longitudinal direction of the diaper, wings having inner and outer surfaces formed on transversely opposite sides of said rear waist region and extending outward in a transverse direction intersecting said longitudinal direction, said fastener sections formed on said wings and extending outward in said transverse direction and being folded back, with inner surfaces thereof inside, in said transverse direction so that male mechanical fastener members attached to inner surfaces of said fastener sections contact with inner surfaces of said wings, said process comprising the steps of:

forming at least said inner surfaces of said wings from a nonwoven fabric comprising a plurality of fibers; and locally pressing said nonwoven fabric from the inner surfaces of the wings toward the outer surfaces of the wings so that discrete portions of the nonwoven fabric contact with said male mechanical fastener members and a portion of said plurality of fibers forming said nonwoven fabric partially protrude toward said male mechanical fastener members and releasably engage a portion of a plurality of hooks forming said male mechanical fastener members.

3. The process according to claim 2, wherein said step of locally pressing said nonwoven fabric further comprises heating at least a portion of said nonwoven fabric.

4. The diaper according to claim 1, wherein discrete regions of said nonwoven fabric are engaged with said hooks, and an intercentral distance between adjacent ones of said discrete engaged regions is at least 5 mm.

* * * * *